United States Patent [19]

Kamimae et al.

[11] 4,394,376

[45] Jul. 19, 1983

[54] METHOD FOR PREVENTING HYPERTRIGLYCERIDEMIA

[75] Inventors: Hiroshi Kamimae, Yokohama; Tadashi Ishikawa, Sagamihara, both of Japan

[73] Assignee: Nihon Nosan Kogyo K.K., Yokohama, Japan

[21] Appl. No.: 351,176

[22] Filed: Feb. 22, 1982

[30] Foreign Application Priority Data

Feb. 25, 1981 [JP] Japan ................................ 56-025428

[51] Int. Cl.$^3$ ............................................. A61K 33/18
[52] U.S. Cl. ..................................................... 424/150
[58] Field of Search ........................................ 424/150

[56] References Cited

PUBLICATIONS

Chemical Abstracts, 89:22749r, (1978), [Ishikawa et al., Japan Kokai 7824,065, 3/6/78].
Chemical Abstracts, 94:82806v, (1981), [Nihon, Japan Kokai 80 150,859, 11/25/80].
Chemical Abstracts, 96:121566e, (1982), [Toshin, Japan Kokai 81 154,969, 11/30/81].
Chemical Abstracts, 96:5243y, (1982), [Katamine, et al., Eiyo To Shokuryo 1981, 34(4), 295].
Chemical Abstracts, 96:338853r, (1982), [Ketamine, Ger. Offen. 3,048,700, 9/10/81].
Chemical Abstracts, 96:5417h, (1982), [Ketamine, et al., Eur. Pat. Appl. 35,883, 9/16/81].

Primary Examiner—Richard A. Schwartz
Attorney, Agent, or Firm—Martin Smolowitz

[57] ABSTRACT

A preventive composite for hyperlipemia. An iodine-enriched egg is used as the effective component of the preventive composite. The egg contains 300 to 4,000 μg of iodine. The egg is obtained by feeding a high amount of an iodine compound and/or a seaweed to egg-laying birds so as to transfer the iodine contained therein to eggs of them.

5 Claims, No Drawings

METHOD FOR PREVENTING HYPERTRIGLYCERIDEMIA

This invention relates to a preventive composite for hypertriglyceridemia which may control plasma triglyceride within a normal range, more particularly, to the preventive composite of which the effective component is a special egg containing a high content of iodine.

At present, one of the main causes of death is an adult disease such as apoplexy and myocardium infarction, and it is generally said that these diseases may be caused by a combination of hyperpiesia and hyperlipemia in which serum or plasma cholesterol and triglyceride are increased. Recently, it is especially said that the above diseases are affected by an excess of triglyceride much more than that of cholesterol, and furthermore it is said that the excess of triglyceride may affect other diseases such as diabetes and corpulence. Since a main factor affecting the plasma triglyceride value is the content of daily meals, it is necessary to limit or control intakes of fats and sugars. Especially as to fats, it is most necessary to be careful about the intake of saturated fatty acids.

In view of this, the inventors of the present invention have conducted many studies on how egg composition may be affected by micro-nutrients added to a feed, and on how lipid metabolism may be affected by the egg composition. As the result of such studies, the inventors have found that an egg containing a high amount of iodine, that is to say, an iodine-enriched egg has an effect of decreasing plasma triglyceride, and completed the present invention thereby.

According to the inventors' research, there is no report that iodine itself or an iodine-enriched food or composite are effective in decreasing the plasma triglyceride value. Therefore, the present invention may be considered as a pioneer invention.

The iodine-enriched egg which is the effective component of the preventive composite against hypertriglyceridemia is obtained usually by the following process.

The process comprises adding an iodine-compound, a seaweed and/or processed seaweed to a feed for egg-laying birds in excess of their ordinary iodine requirement, and feeding the egg-laying birds with the feed so that a high amount of iodine contained in the feed is transferred to the eggs which the birds lay. Iodine compounds to be used are, for example, calcium iodate, potassium iodate, sodium iodate, potassium iodide, calcium iodide, sodium iodide, cuprous iodide, thymol iodide, calcium iodobehemate, diiodo-salicyclic acid, calcium periodate. Examples of seaweed containing a high amount of iodine are sea tangle and kelp.

Considering the health of egg-laying birds and the transfer rate of iodine to eggs, calcium iodate is the most desirable iodine compound. It is even more desirable to use calcium iodate and seaweed jointly. The amount of iodine dosed to egg-laying birds may vary according to the species of egg-laying birds such as hens and quails. In general, the iodine compound and/or seaweed are added so that the iodine content of feed is 50 to 2,500 ppm, more preferably, 50 to 150 ppm.

Thus, at about a week after beginning to feed egg-laying birds with the feed containing a high amount of iodine, the birds begin to lay the desired iodine-enriched eggs. For example, when egg-laying hens are fed with a feed containing about 50 ppm of iodine, they lay eggs containing about 300 µg of iodine per egg. And, when egg-laying hens are fed with a feed whose iodine content is about 100 ppm, they lay eggs whose iodine content is about 600 to 800 µg. Egg-laying hens lay eggs whose iodine content is about 4,000 µg, when they are fed with a feed whose iodine content is about 2,500 ppm. The iodine requirement of egg-laying hens is 0.3 to 0.35 mg per kg of feed according to the National Research Council, and indeed an ordinary feed marketed at present contains 0.3 to 2.0 mg per kg of feed. When egg-laying hens are fed with the ordinary feed, they lay ordinary eggs whose iodine content is about 6 to 30 µg. In comparison with the ordinary eggs, the iodine-enriched eggs obtained by the above process contain a remarkably high amount of iodine.

The iodine-enriched eggs may be used as the preventive composite of the present invention in the non-processed state. After separating the yolk from the egg, the yolk alone may be used as the effective component of the preventive composite, as the yolk portion is especially effectual. The iodine-enriched egg and the yolk separated therefrom may also be used after a suitable process, for example, drying, concentrating, powdering or granulating. They further may be used in the form of a tablet or powdered medicine by mixing with a variety of mass or bonding agents. Furthermore, they can be used in the form of an extract, drinkable, syrup or emulsion.

The iodine-enriched eggs can be used as the preventive composite with safety, because the egg-laying bird's body acts as a live filter. The preventive composite of the present invention is dosed or ingested so that the iodine dosage is about 300 to 1,000 µg per day. When the present composite is continuously dosed to a person whose plasma triglyceride value is high, the value is lowered. And, even if sugars or fats are ingested in small excess of the required amount, the plasma triglyceride value is never heightened owing to continuous dosing of the present composite. In this way, hypertriglyceridemia is surely prevented. The preventing effect is caused by the fact that the amount of lactic acid produced is kept at a low level, and the fact that free fatty or lipidic acids and triglycerides are ingested or utilized in muscles and other histology or tissue.

Animal experiments and clinical experiments were done on the effect of the present composite for decreasing plasma triglyceride or preventing hypertriglyceridemia. Results of these experiments are as follows:

Experiment 1

Fourteen (14) male rats of Wistar decent whose body weight was about 80 to 90 g were divided into two groups of seven (7) heads each, and fed at 22±1° C. temperature and 50 to 60% humidity. One of the groups, designated as a test group, was fed with a solid test feed which was prepared by adding 1% of powdered iodine-enriched egg of Example 2 mentioned later to a marketed feed for rats. The other group, designated as a control group, was fed with a solid control feed prepared by adding 1% of powdered ordinary egg to the marketed feed for rats. Both of the groups were fed for forty-three days, and then the serum or plasma triglyceride of the rats was measured. The present composite was proved to be effective in decreasing the plasma triglyceride value as shown in Table 1.

TABLE 1

| Rat No. | Plasma triglyceride value (mg/dl) | |
|---|---|---|
| | Test Group | Control Group |
| 1 | 58 | 61 |
| 2 | 75 | 123 |
| 3 | 88 | 146 |
| 4 | 64 | 97 |
| 5 | 66 | 89 |
| 6 | 47 | 92 |
| 7 | Not measured | 124 |
| Average ± S.D | 66 ± 14 | 105 ± 28 |

Experiment 2

A test group of three Arabian horses three years of age was fed for two months with a test feed prepared by adding 1% of powdered iodine-enriched egg of the Example 2 to a marketed feed for horses. A control group of three Arabian horses three years of age was fed for two months with the above marketed feed to which no powdered egg was added. The lactic acid value and triglyceride value were measured as shown in Table 2. In comparison with the control group, the triglyceride value of the test group was never increased, the amount of lactic acid produced was decreased.

TABLE 2

| | Before Test | | | | After a month | | | | | | (mg/dl) After two months | | | | | |
|---|---|---|---|---|---|---|---|---|---|---|---|---|---|---|---|---|
| | Before Training | | 5 minutes after Training | | Before Training | | 5 minutes after Training | | 30 minutes after Training | | Before Training | | 5 minutes after Training | | 30 minutes after Training | |
| | L.A. | T.G. | L.A. | T.G. | L.A. | T.G. | L.A. | T.G. | L.A. | T.G. | L.A. | T.G. | L.A. | T.G. | L.A. | T.G. |
| Test Group | 21 | 20 | 30 | 18 | 15 | 25 | 23 | 18 | 19 | 25 | 24 | 19 | 28 | 16 | 27 | 19 |
| Control Group | 21 | 25 | 35 | 24 | 21 | 32 | 42 | 26 | 22 | 33 | 26 | 28 | 43 | 23 | 33 | 28 |

*L.A.—Lactic Acid
T.G.—Triglyceride
*Each value is the average value of three horses.

Experiment 3

Five persons ate ordinary eggs for two weeks at the rate of three eggs per day, and thereafter the plasma triglyceride value was measured before breakfast. Then, the same persons ate iodine-enriched eggs of Example 1 mentioned later for two weeks at the rate of three eggs per day, and thereafter the plasma triglyceride value was again measured before breakfast. They continued to have ordinary meals in addition to the ordinary eggs or the iodine-enriched eggs.

The present composite of iodine-enriched egg was proved to have an effect of decreasing the plasma triglyceride value as to the persons Nos. 1, 4 and 5, and the effect of preventing hypertriglyceridemia in persons Nos. 2 and 4, as shown in Table 3.

TABLE 3

| Person No. | Plasma triglyceride after eating ordinary eggs for two weeks (mg/dl) | Plasma triglyceride after eating iodine-enriched eggs for two weeks (mg/dl) |
|---|---|---|
| 1 | 167 | 126 |
| 2 | 92 | 85 |
| 3 | 79 | 65 |
| 4 | 197 | 135 |
| 5 | 115 | 88 |

Experiment 4

Male rats of SD descent and four weeks old were fed with a meal-feeding twice a day (at 8 to 9 o'clock and 20 to 21 o'clock), and caused to do voluntary running in rotary cages from the age of six weeks. At the age of seven weeks, they were divided into a test group and a control group. Rats of the test group were fed with a powdered test feed prepared by adding 1.5% of powdered iodine-enriched egg of Example 2 to a marketed feed for rats, while rats of the control group were fed with a powdered control feed prepared by adding 1.5% of powdered ordinary egg to the above marketed feed. At the age of eight months, blood drawing from caudal veins was done as to each eight rats of the test group and the control group at 8 o'clock (rats being in the state of fasting) and at 13 o'clock, and they were slaughtered by head-cutting at 20 o'clock. There was no difference between the test group and the control group in regards to body weight increase, feed ingestion, voluntary running amount and viscera weight at slaughtering.

In comparison with the control group, the plasma triglyceride value of the test group was clearly decreased as shown in Table 4.

TABLE 4

| Time of day (hrs.) | Plasma triglyceride (mg/100 ml) | |
|---|---|---|
| | Test Group | Control Group |
| 8 | 127.8 ± 16.8 | 157.7 ± 16.8 |
| 13 | 164.0 ± 20.5 | 230.8 ± 21.5 |
| 20 | 110.5 ± 11.7 | 155.5 ± 17.1 |

Furthermore, at the age of ten months, hepaticintestinal triglyceride secretion rate (TGSR) and plasma triglyceride removal rate (TGRR) were measured as to each five rats of the test group and the control group. While the TGSR of the test group was lower than that of the control group, the TGRR of the test group was higher than that of the control group, as shown in Table 5. Therefore, the composite of the present invention was proved to have the effect of decreasing the plasma triglyceride value.

TABLE 5

| | TGSR | | TGRR | |
|---|---|---|---|---|
| | mg/min/rat | µg/min/100g B.W. | mg/min/rat | µg/min/100g B.W. |
| Control Group | 2.35 ± 0.06 | 408.5 ± 6.4 | 1.44 ± 0.16 | 254.0 ± 24.8 |
| Test Group | 1.93 ± 0.11 | 355.6 ± 17.7 | 1.84 ± 0.13 | 238.5 ± 17.1 |

EXAMPLE 1

Calcium iodate was added to a marketed feed for hens so that the iodine content became 100 ppm, and the feed was fed to hens which had begun to lay eggs four months before. Thus, seven days after the feeding, the hens laid iodine-enriched eggs containing 550 μg of iodine per egg on an average.

EXAMPLE 2

Calcium iodate was added to a hen's feed on the market so that the iodine content was 2,000 ppm, and powdered seaweed was further added to the admixture in the amount of 1%. The feed was fed to hens of 100 heads that had begun to lay eggs five months before. The iodine-enriched eggs of 150 kg obtained by the said feeding were dried with a spray-dryer, and thereby 32 kg of the present composite were produced. The composite in the form of powdered egg contained 212 mg of iodine per kg of composite.

EXAMPLE 3

Sodium iodide was added to a marketed feed for hens so that the iodine content was 150 ppm, and then there were obtained eggs containing 1,300 μg per egg on an average by the same process as in Example 1. The iodine-enriched eggs were then broken, and divided into the yolk and the albumen. Thereafter, 10 kg of dextrin were added to 50 kg of the yolk, and then they were mixed fully and spray-dried by a spray-drying apparatus, whereby 31 kg of the composite were obtained.

We claim:

1. A method for preventing hypertriglyceridemia in humans comprising ingesting a hypertriglyceridemia preventing amount of iodine-enriched whole egg or egg yolk in the daily diet.

2. The method of claim 1, wherein the amount of egg or egg yolk ingested is selected so that the amount of iodine dosage is about 300 to 1650 μg per day.

3. The method of claim 2, wherein the dosage is about 300 to 1000 μg per day.

4. The method according to any one of claims 1 to 3, wherein the egg is obtained by feeding an iodine-containing material selected from the group consisting of iodine-containing compounds and seaweed and mixtures thereof to egg-laying birds in excess of their ordinary iodine requirement.

5. The method according to any one of claims 1 to 3, wherein the egg is in the form of a tablet, powder, extract, syrup or emulsion.

* * * * *